US009084698B2

(12) United States Patent
Ichikawa et al.

(10) Patent No.: US 9,084,698 B2
(45) Date of Patent: Jul. 21, 2015

(54) ABSORBENT ARTICLE WITH FOLDED LIQUID-ABSORBENT STRUCTURE

(75) Inventors: Makoto Ichikawa, Kagawa (JP); Kenichi Sasayama, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 910 days.

(21) Appl. No.: 13/260,805

(22) PCT Filed: Feb. 22, 2010

(86) PCT No.: PCT/JP2010/052594
§ 371 (c)(1),
(2), (4) Date: Sep. 28, 2011

(87) PCT Pub. No.: WO2010/113562
PCT Pub. Date: Oct. 7, 2010

(65) Prior Publication Data
US 2012/0035576 A1    Feb. 9, 2012

(30) Foreign Application Priority Data

Mar. 31, 2009  (JP) ................ 2009-086867

(51) Int. Cl.
*A61F 13/15* (2006.01)
*A61F 13/20* (2006.01)
(Continued)

(52) U.S. Cl.
CPC ......... *A61F 13/49001* (2013.01); *A61F 13/495* (2013.01); *A61F 13/496* (2013.01);
(Continued)

(58) Field of Classification Search
CPC ................ A61F 13/55115; A61F 13/49001; A61F 13/53436; A61F 13/539; A61F 13/4704; A61F 13/47218; A61F 13/53409

USPC .......... 604/385.01, 385.24, 400, 402
See application file for complete search history.

(56) References Cited

U.S. PATENT DOCUMENTS 2,952,260 A * 9/1960 Burgeni ................. 604/374
3,653,382 A   4/1972 Easley et al.
(Continued)

FOREIGN PATENT DOCUMENTS

EP       1457185 A1   9/2004
JP       06-167001 A  6/1994
(Continued)

OTHER PUBLICATIONS

International Search Report for PCT/JP2010/052594 mailed May 18, 2010.

(Continued)

*Primary Examiner* — Michele M Kidwell
(74) *Attorney, Agent, or Firm* — Lowe Hauptman & Ham, LLP

(57) ABSTRACT

A diaper has an outer sheet and a crotch member which includes a pair of skin-contactable sheets spaced from each other in a transverse direction. Inner side edges of the respective skin-contactable sheets cooperate with respective second ends of front and rear waist members to define an opening. A plurality of crotch elastic members is attached to the inner side edges. Under the effect of these crotch elastic members, a length dimension of the skin-contactable sheets is substantially reduced. The inner side edges of the skin-contactable sheets are spaced from the outer sheet in a thickness direction to form a space between the skin-contactable sheets and the outer sheet. A liquid-absorbent structure is provided in the space and includes a fold formed by folding the structure along a folding line. A top of the fold is bonded to the inner side edges of the respective skin-contactable sheets.

12 Claims, 10 Drawing Sheets

(51) Int. Cl.

| | |
|---|---|
| *A61F 13/49* | (2006.01) |
| *A61F 13/494* | (2006.01) |
| *A61F 13/495* | (2006.01) |
| *A61F 13/496* | (2006.01) |
| *A61F 13/64* | (2006.01) |
| *A61F 13/534* | (2006.01) |

(52) U.S. Cl.
CPC ..... *A61F13/49011* (2013.01); *A61F 13/49426* (2013.01); *A61F 13/53409* (2013.01); *A61F 13/64* (2013.01)

(56) References Cited

U.S. PATENT DOCUMENTS

| | | | | |
|---|---|---|---|---|
| 3,943,930 | A * | 3/1976 | Schaar | 604/365 |
| 5,370,632 | A | 12/1994 | Beplate | |
| 6,165,160 | A * | 12/2000 | Suzuki et al. | 604/385.201 |
| 6,423,042 | B1 | 7/2002 | Sasaki | |
| 6,475,199 | B1 * | 11/2002 | Gann et al. | 604/385.01 |
| 6,506,185 | B1 | 1/2003 | Sauer et al. | |
| 6,638,260 | B2 * | 10/2003 | Mishima | 604/385.01 |
| 7,033,341 | B2 * | 4/2006 | Mishima | 604/385.01 |
| 7,666,173 | B2 * | 2/2010 | Mishima et al. | 604/385.19 |
| 8,029,486 | B2 * | 10/2011 | Nakajima et al. | 604/385.19 |
| 2002/0068920 | A1 * | 6/2002 | Mishima | 604/385.28 |
| 2002/0173763 | A1 * | 11/2002 | Tsuji et al. | 604/385.19 |
| 2003/0045855 | A1 | 3/2003 | Ono et al. | |
| 2004/0002689 | A1 | 1/2004 | Igaue et al. | |
| 2004/0039363 | A1 * | 2/2004 | Sugiyama et al. | 604/385.101 |
| 2004/0127864 | A1 * | 7/2004 | Sugito | 604/346 |
| 2005/0228357 | A1 * | 10/2005 | Mishima et al. | 604/385.19 |
| 2005/0228358 | A1 | 10/2005 | Mishima et al. | |
| 2005/0267436 | A1 * | 12/2005 | Mishima et al. | 604/385.19 |
| 2007/0106240 | A1 * | 5/2007 | Nakajima et al. | 604/385.19 |
| 2007/0239128 | A1 * | 10/2007 | Takada et al. | 604/385.25 |
| 2010/0063471 | A1 * | 3/2010 | Minato et al. | 604/385.23 |

FOREIGN PATENT DOCUMENTS

| | | |
|---|---|---|
| JP | 3205690 B2 | 6/2001 |
| JP | 2002-017779 A | 1/2002 |
| JP | 2003-265533 A | 9/2003 |
| JP | 2006-116157 A | 5/2006 |
| JP | 3954060 B2 | 5/2007 |
| JP | 2007-275298 A | 10/2007 |
| WO | 0115650 A1 | 3/2001 |

OTHER PUBLICATIONS

Corresponding EP10758339.5 Search Report dated May 2, 2013.

* cited by examiner

ABSORBENT ARTICLE WITH FOLDED LIQUID-ABSORBENT STRUCTURE

RELATED APPLICATIONS

The present application is a National Phase of International Application Number PCT/JP2010/052594, filed Feb. 22, 2010 and claims priority from, Japanese Application Number 2009-086867, filed Mar. 31, 2009.

TECHNICAL FIELD

The present invention relates to absorbent articles and more particularly to absorbent articles such as disposable diapers, toilet-training pants or incontinent briefs.

BACKGROUND

Examples of absorbent articles each including an absorbent structure adapted to absorb bodily fluids are known, for example, from disclosures of the JP 2002-17779 A (PTL 1) and JP 3954060 B2 (PTL 2). In the absorbent article disclosed in PTL 1, an absorbent structure is provided on the skin-facing side of a liquid-impervious outer sheet. The outer sheet and the absorbent structure are partially bonded to each other to leave a space between the outer sheet and the absorbent structure and thereby to assure that bodily fluids can be absorbed by the absorbent structure also from its outer sheet-facing side. In the absorbent article disclosed in PTL 2, a sheet-like leakage-proof barrier member defines a bottom zone and lateral zones adapted to rise from both sides of the bottom zone toward the wearer's skin so that these bottom and lateral zones define an internal space. An absorbent structure is provided within this internal space and absorbs bodily fluids discharged into the internal space.

CITATION LIST

Patent Literature

{PTL 1} JP 2002-17779 A
{PTL 2} JP 3954060 B2

SUMMARY

Technical Problem

In both cases of PTL 1 and PTL 2, the absorbent structure is attached to the outer sheet facing away from the wearer's skin. When a certain amount of bodily fluids has been absorbed by the absorbent structure, the absorbent structure comes in close contact with the outer sheet since its weight has increased due to such absorbed bodily fluids and there is no more space between the absorbent structure and the outer sheet to receive any additional amount of bodily fluids. In consequence, after the absorbent structure has absorbed a certain amount of bodily fluids, additional bodily fluids can be absorbed by the absorbent structure only from the skin-facing side thereof. Specifically, it becomes difficult for absorbent material lying on the outer sheet-facing side of the absorbent structure to absorb bodily fluids, i.e., to be efficiently utilized.

An object of the present invention is to provide an absorbent article improved so that bodily fluids can be absorbed by the absorbent structure from the skin-facing side of the absorbent structure as well as the non-skin-facing side and thereby a liquid-absorbent core can be efficiently utilized.

Solution to Problem

According to the present invention, there is provided an absorbent article having a longitudinal direction and a transverse direction, and including:

a chassis including a skin-facing side, a non-skin-facing side, a front waist region, a rear waist region and a crotch region extending between these front and rear waist regions;

a liquid-absorbent structure extending at least in the crotch region to absorb bodily fluids and including a liquid-absorbent core and a liquid-pervious wrapping sheet adapted to wrap the liquid-absorbent core.

According to the present invention, the chassis further includes a skin-contactable sheet lying on the skin-facing side to define at least the crotch region and formed with a liquid-pervious region for bodily fluids, a liquid-impervious outer sheet lying on the non-skin-facing side and spacer means adapted to space the skin-contactable sheet from the outer sheet and thereby to define an space therebetween and the liquid-absorbent structure is positioned within the space and directly or indirectly connected to the skin-contactable sheet in alignment with the liquid-pervious region in a thickness direction wherein a part of the liquid-absorbent structure is capable of coming in contact with the outer sheet.

The present invention includes embodiments as will be described below.

A substantial length dimension of the skin-contactable sheet in the longitudinal direction is smaller than a length dimension of the outer sheet in the longitudinal direction under the effect of the spacer means.

The liquid-pervious region is defined by an opening formed in the skin-contactable sheet and the skin-contactable sheet is elasticized along the opening at least in the longitudinal direction under the effect of the spacer means.

A length dimension of the liquid-absorbent structure in the longitudinal direction is substantially larger than a length dimension of the skin-contactable sheet in the longitudinal direction and substantially smaller than a length dimension of the outer sheet in the longitudinal direction and the liquid-absorbent structure includes front and rear ends extending in the transverse direction and formed with first bonded regions in which the liquid-absorbent structure is bonded to the skin-contactable sheet and side edges extending in the longitudinal direction and formed with non-bonded regions in which the liquid-absorbent structure can be spaced from the skin-contactable sheet.

The liquid-absorbent structure is formed along the side edges thereof with second bonded regions lying in the crotch region wherein the liquid-absorbent structure is bonded to the skin-contactable sheet in the second bonded regions.

The skin-contactable sheet includes a fold formed along a folding line extending in the transverse direction and a fold-bonding region defined on inner surface of the fold wherein mutually opposed halves of the inner surface are bonded together in the bonded region.

The fold is formed in the crotch region to extend toward the outer sheet in a thickness direction.

The absorbent article further including a connector extending across the opening in the transverse direction X and connecting transversely opposite points on a periphery of the opening.

The connector lies at least in the crotch region.

The fold-bonding region in which the mutually opposed halves of the inner surface of the fold are bonded together overlaps the connector in the thickness direction.

Advantageous Effects of Invention

The absorbent article includes the skin-contactable sheet defining the crotch region of the chassis, the outer sheet and the spacer means serving to space these skin-contactable sheet and the outer sheet from each other in the thickness direction and thereby to define the space. The liquid-absorbent structure is provided within this space so that only a part thereof can come in contact with the outer sheet but the rest is slung within the space defined between the skin-contactable sheet and the outer sheet without coming in contact with the outer sheet. As a consequence, even when the weight of the liquid-absorbent structure increases due to bodily fluids absorbed therein, it is assured that the space is maintained. This means that bodily fluids can be absorbed by the liquid-absorbent structure not only through the skin-contactable sheet-facing side thereof but also through the outer sheet-facing side thereof. Absorption of bodily fluids through both sides of the liquid-absorbent structure allows the core to be efficiently utilized and thereby allows bodily fluids to be rapidly absorbed. In this way, leak of bodily fluids can be reliably restricted.

DESCRIPTION OF EMBODIMENTS

{Embodiment 1}

Figure 1:
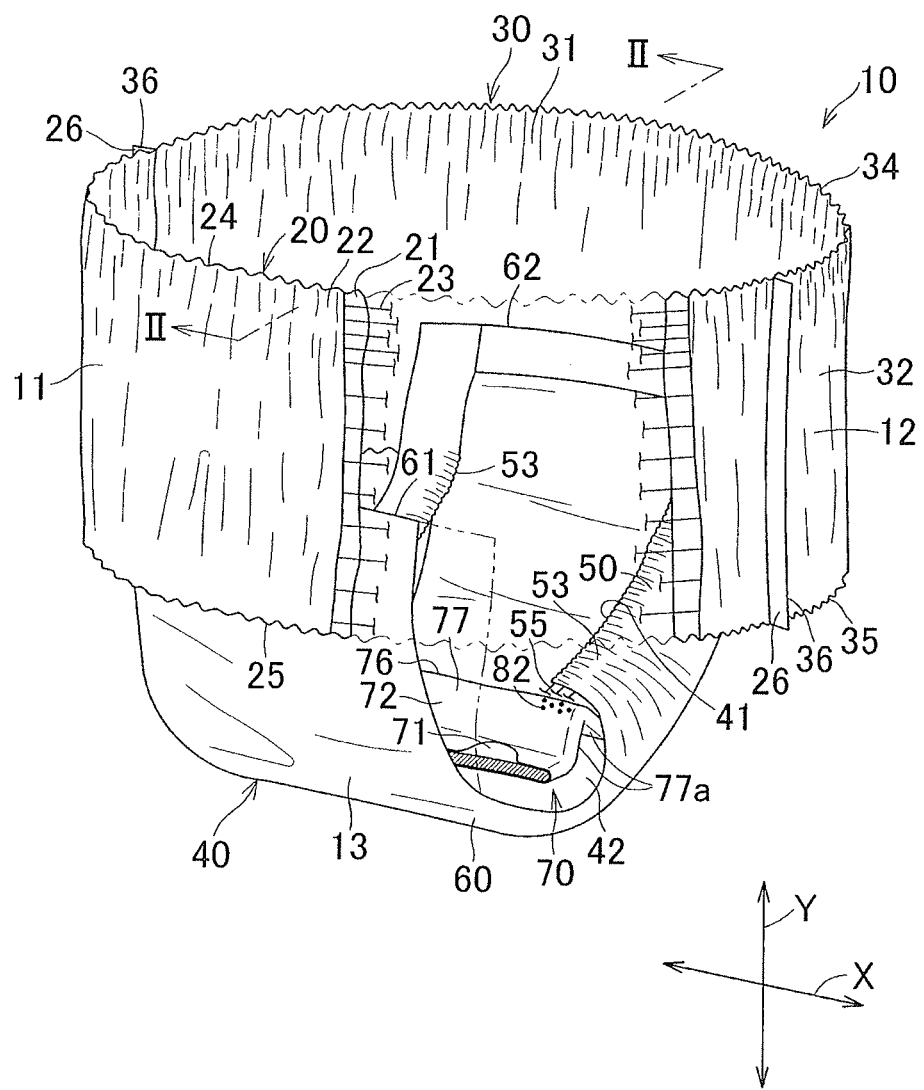
{FIG 1} A perspective view showing a diaper according to Embodiment 1.
Figure 2:
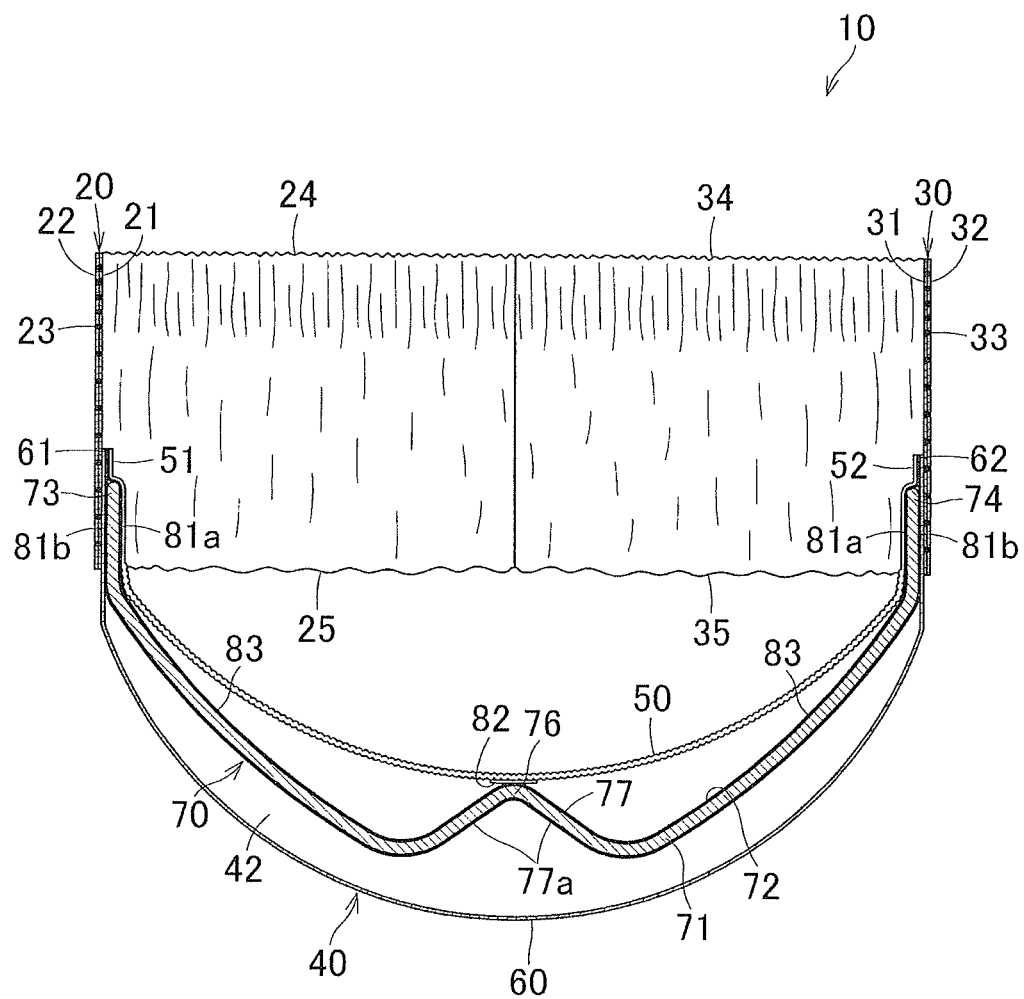
{FIG 2} A sectional view taken along the line II-II in FIG. 1.
Figure 3:
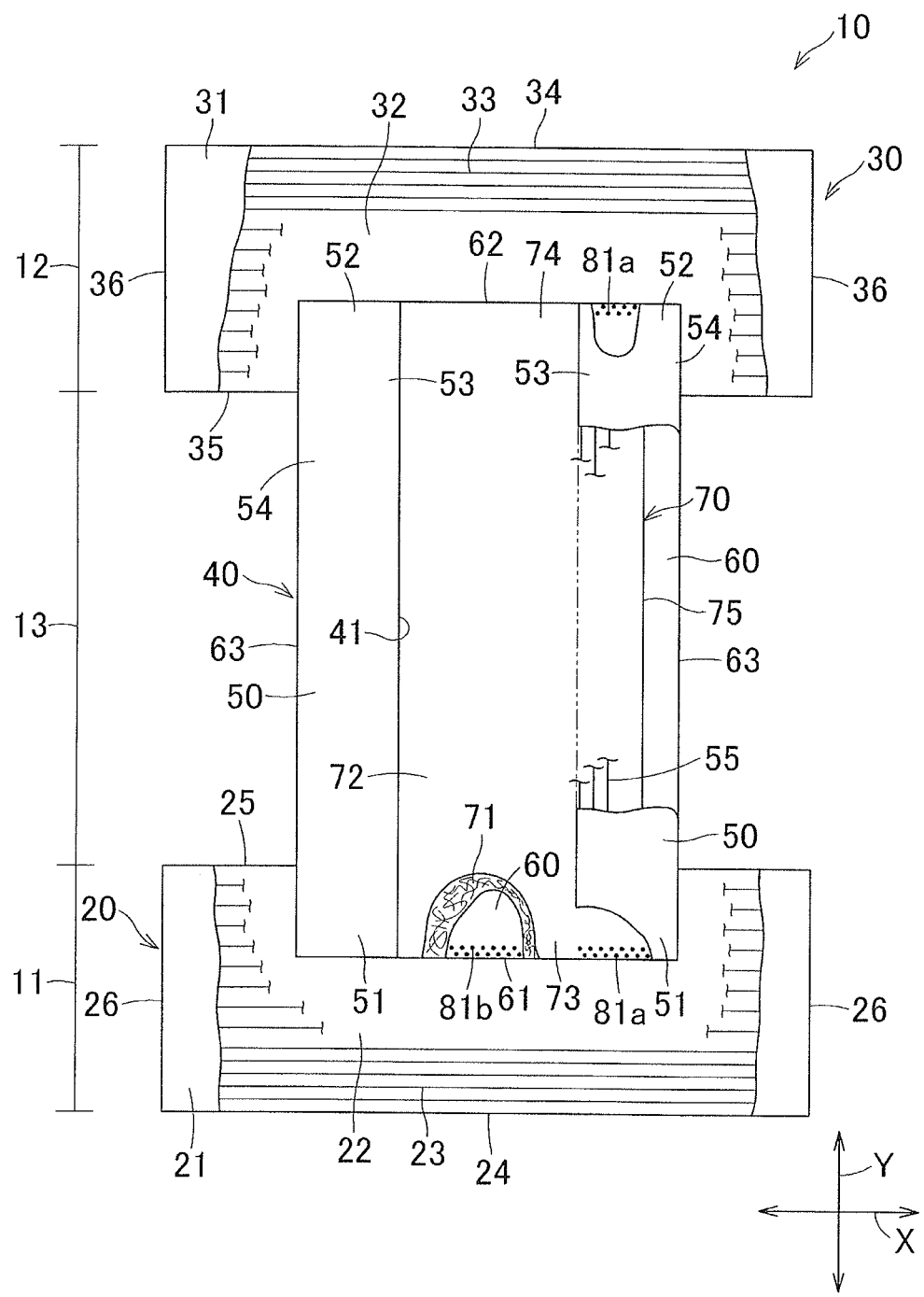
{FIG 3} A plan view showing the diaper of FIG. 1 as having been flatly developed.

One embodiment of the absorbent article according to the present invention in the form of a disposable diaper will be described with reference to the accompanying drawings. FIGS. 1 through 3 illustrate Embodiment 1 of the present invention wherein FIG. 1 is a perspective view showing the diaper 10 according to Embodiment 1, FIG. 2 is a sectional view taken along the line II-II in FIG. 1 and FIG. 3 is a plan view showing the diaper 10 of FIG. 1 as having been flatly developed. FIGS. 1 and 3 are partially cutaway for convenience of illustration. In FIG. 3, respective elastic members are shown as contractile force thereof being restricted.

The diaper 10 has a longitudinal direction Y and a transverse direction X and includes a skin-facing side, a non-skin-facing side, a front waist region 11, a rear waist region 12 and a crotch region 13 extending between these front and rear waist regions 11, 12. The front waist region 11 is formed of a front waist member 20, the rear waist region 12 is formed of a rear waist member 30 and the crotch region 13 is formed of a crotch member 40. By the respective members 20, 30, 40, a herein-called chassis is configured.

The front and rear waist members 20, 30 respectively include inner sheets 21, 31 each defining a skin-facing side, outer sheets 22, 32 each defining a non-skin-facing side and elastic members 23, 33 attached to front and rear waist members 20, 30, respectively. The front waist member 20 is contoured by its first and second ends 24, 25 extending in the transverse direction X and its both side edges 26, 26 extending in the longitudinal direction Y. In a similar fashion, the rear waist member 30 is contoured by its first and second ends 34, 35 extending in the transverse direction X and its both side edges 36, 36 extending in the longitudinal direction Y. The side edges 26, 26 of the front waist region are joined to the associated side edges 36, 36 of the rear waist region so that the front and rear waist members 20, 30 cooperate with each other to form an annular waist member. The respective first ends 24, 34 of the front and rear waist members 20, 30 annularly joined together in this manner define a waist-opening.

The elastic members 23, 33 for the front and rear waist members are sandwiched between the inner and outer sheets 21, 22 and between the inner and outer sheets 31, 32 and bonded under tension, i.e., contractibly to at least one of the inner and outer sheets 21, 22 and to at least one of the inner and outer sheets 31, 32. The elastic members 23, 33 for the front and rear waist members, respectively, serve to elasticize the front and rear waist members 20, 30 in the transverse direction X. Respective pitches of the elastic members 20, 30 for the front and rear waist members in the longitudinal direction Y may be set to be relatively small in vicinities of the first ends 24, 34 and relatively large in vicinities of the second ends 25, of the front and rear waist regions. By setting the pitch to be relatively small in vicinities of the first ends 24, 34, it is possible to prevent the diaper 10 from slipping down along the wearer's waist. By setting the pitch to be relatively large in vicinities of the second ends 25, 35, a tensile stress generated in a region extending below the waist-opening can be appropriately restricted to prevent this lower region from excessively compressing the wearer's body without leaving a clearance between this region and the wearer's body which might lead to leakage of bodily fluids.

The crotch member 40 includes a skin-contactable sheet 50 defining the skin-facing side and a outer sheet 60 defining the garment-facing side wherein the outer sheet 60 is opposed to and bonded to the inner sheets 21, 31 of the front and rear waist members 20, 30 to form a pant-shape as a whole. The crotch member 40 and the front and rear waist members 20, 30 are bonded together by the intermediary of bonding regions (not shown) formed, for example, by adhesive.

Both the skin-contactable sheet 50 and the outer sheet 60 are liquid-impervious and specifically formed of a laminate of liquid-impervious film and a fibrous non-woven fabric. Considering the texture of these sheets, the fibrous non-woven fabric of the laminate is preferably facing the wearer's skin.

The outer sheet 60 is contoured by its front and rear ends 61, 62 extending in the transverse direction X and its both side edges 63, 63 extending in the longitudinal direction Y. The skin-contactable sheet 50 includes a pair of belts spaced from each other in the transverse direction X, each being contoured by its front and rear ends 51, 52 extending in the transverse direction X and its inner and outer side edges 53, 54 extending in the longitudinal direction Y. In this embodiment using a pair of the skin-contactable sheets 50 spaced from each other in the transverse direction X, respective inner side edges 53, 53 thereof cooperate with the respective second ends 25, 35 of the front and rear waist members to define an opening 41 according to the present invention. This opening 41 is formed in the crotch region 13 serving to guide flow of bodily fluids such as urine toward the outer sheet 60. While the opening 41 is defined by a pair of the skin-contactable sheets 50 as in this embodiment, it is also possible to cut out the opening 41 from a continuous sheet or to use a liquid-pervious sheet as a skin-contactable sheet without forming the skin-contactable sheet with such opening 41 so far as bodily fluids are able to permeate the skin-contactable sheet or sheets 50 toward the liquid-absorbent structure 70.

In the state free from effects of the respective elastic members, the skin-contactable sheets 50 and the outer sheet 60 have substantially the same length dimension in the longitudinal direction Y and the outer side edges 54 of the respective skin-contactable sheets are bonded to the associated side edges 63 of the outer sheet. In addition, the front and rear ends 51, 52 of the respective skin-contactable sheets also are bonded to the front and rear ends 61, 62 of the outer sheet, respectively. The skin-contactable sheets 50 are provided along its inner side edges 53 with a plurality of crotch elastic members 55 attached thereto under tension to be contractible. These crotch elastic members 55 elasticize the skin-contactable sheets 50 in the longitudinal direction Y. Upon contraction of the crotch elastic members 55, Length dimension of the skin-contactable sheets 50 in the longitudinal direction Y is substantially reduced.

When the substantial length dimension of the skin-contactable sheets 50 in the longitudinal direction Y become shorter than that of the outer sheet 60 as has been described just above, the inner side edges 53, 53 of the skin-contactable sheets are spaced upward from the outer sheet 60 in the thickness direction and a space 42 is formed between the skin-contactable sheets 50 and the outer sheet 60 (See FIGS. 1 and 2). The crotch elastic members 55 constitute a part of spacer means according to the present invention.

The liquid-absorbent structure 70 is provided within the space 42 defined between the skin-contactable sheets 50 and the outer sheet 60. The liquid-absorbent structure 70 includes a liquid-absorbent core 71 adapted to absorb bodily fluids and a wrapping sheet 72 adapted to wrap the liquid-absorbent core 71. The wrapping sheet 72 is liquid-pervious and entirely wraps the core 71. In other words, the liquid-absorbent structure 70 is adapted to absorb bodily fluids such as urine in its entire area including both its upper and lower surfaces as viewed in its thickness direction. Such liquid-absorbent structure 70 is provided in the form of a relatively thin sheet wherein, for example, a mixture of fluff pulp fibers and superabsorbent polymer particles may be used as the liquid-absorbent core 71 and a liquid-pervious non-woven fabric may be used as the wrapping sheet 72.

The liquid-absorbent structure 70 is contoured by its front and rear ends 73, 74 extending in the transverse direction X and its side edges 75, 75 extending in the longitudinal direction Y. A length dimension of the liquid-absorbent structure 70 in the longitudinal direction Y is substantially the same as that of the skin-contactable sheets 50 and the outer sheet 60 in the state of the diaper 10 free from effects of the respective elastic members as seen in FIG. 3. The liquid-absorbent structure 70 is provided between the skin-contactable sheets 50 and the outer sheet 60 with the front and rear ends 73, 74 bonded to the front and rear ends 51, 52 of the respective skin-contactable sheets 50 and the front and rear ends 61, 62 of the outer sheet 60, respectively, in the associated first bonded regions 81a, 81b. It should be appreciated here that the front and rear ends 73, 74 may be directly or indirectly bonded at least to the front and rear ends 51, 52 of the skin-contactable sheets 50.

The liquid-absorbent structure 70 includes a fold 77 formed along a folding line 76 extending in the transverse direction X. The folding line 76 is defined by a transverse center line bisecting a length dimension of the liquid-absorbent structure 70 in the longitudinal direction Y. The fold 77 has its inner surface 77a folded into two halves opposed to each other and has its top bonded to the inner side edges 53 of the respective skin-contactable sheets 50 to form second bonded regions 82. The liquid-absorbent structure 70 is not bonded to the skin-contactable sheets 50 and the outer sheet 60 in regions other than the first and second bonded regions 81a, 81b, 82 to define non-bonded regions 83 adapted to be spaced from these sheets 50, 60.

By folding the liquid-absorbent structure 70 along the folding line 76, the length dimension thereof in the longitudinal direction Y can be substantially reduced so as to be larger than that of the respective skin-contactable sheets and smaller than that of the outer sheet 60. More specifically, when the state of the diaper is changed from the state of FIG. 3 to the state of FIGS. 1 and 2 in which the diaper is put on the wearer's body, the liquid-absorbent structure 70 sags within the space 42 under contractile force of the respective elastic members to make the substantial dimension of the respective skin-contactable sheets 50 smaller than that of the outer sheet 60. Consequentially, the substantial dimension of the liquid-absorbent structure 70 interposed between the skin-contactable sheets 50 and the outer sheet 60 becomes larger than that of the respective skin-contactable sheets and smaller than that of the outer sheet 60.

The liquid-absorbent structure 70 has a face-to-face positional relation with the opening 41 in the thickness direction. Specifically, the liquid-absorbent structure 70 is positioned just below the opening 41 contoured by the skin-contactable sheets 50 in face-to-face relation with but spaced from the liquid-absorbent structure 70 to define a space.

With such diaper 10 put on the wearer's body in the state as shown in FIGS. 1 and 2, the respective skin-contactable sheets 50 have the substantial length dimension in the longitudinal direction Y smaller than that of the outer sheet 60 and, in addition to this relationship of the substantial dimensions, the crotch elastic members 55 bonded under tension to the inner side edges 53, 53 of the respective skin-contactable sheets 50 further ensure that the space 42 is defined between the skin-contactable sheets 50 and the outer sheet 60. The liquid-absorbent structure 70 provided within the space 42 has its substantial length dimension in the longitudinal direction Y which is larger than that of the respective skin-contactable sheets 50 but smaller than that of the outer sheet 60 and the front and rear ends 73, 74 of the liquid-absorbent structure 70 are sandwiched and bonded between the front and rear ends 51, 52 of the respective skin-contactable sheets 50 and the front and rear ends 61, 62 of the outer sheet 60, respectively. In this way, the liquid-absorbent structure 70 is slung within the space 42 like a hammock. Furthermore, the liquid-absorbent structure 70 has its fold 77 formed substantially in the middle thereof in the longitudinal direction Y and bonded to the respective skin-contactable sheets 50 in the second bonded regions 82. With such arrangement, the non-bonded regions 83 are slung down from the second bonded regions 82 toward the outer sheet 60. The second bonded regions 82 allow it to prevent the liquid-absorbent structure 70 from coming in contact with the outer sheet 60 and thereby to maintain the space between the liquid-absorbent structure 70 and the outer sheet 60.

Bodily fluids such as urine discharged onto the diaper 10 flow through the opening 41 defined between the skin-contactable sheets 50 and finally flow into the space 42 formed between the liquid-absorbent structure 70 and the outer sheet 60. Specifically, after the flow of urine reached the liquid-absorbent structure 70 provided below the opening 41 as viewed in the thickness direction, a part of urine is absorbed by the liquid-absorbent structure 70 through it upper surface facing the skin-contactable sheets 50 and the rest of urine flows down along the side edges 75 of the liquid-absorbent structure 70 toward the outer sheet 60 and is retained in the space 42 defined by the outer sheet 60 which is sufficiently liquid-impervious. If the amount of urine retained in the space 42 increases until it comes in contact with the liquid-absorbent structure 70, this increased amount of urine begins to be absorbed by the liquid-absorbent structure 70 through its lower surface facing the outer sheet 60. Even if the space 42 collapses as the wearer gets seated, any remaining amount of urine retained in the space 42 comes in contact with and absorbed by the liquid-absorbent structure 70 through its lower surface.

For the reason that urine can be temporarily retained in the space 42 and then absorbed by the liquid-absorbent structure 70 in the manner as has been described just above, urine can be reliably absorbed and retained to be prevented from leaking from the diaper 10 even when a liquid-absorbent core having relatively low absorption rate is used. Particularly when a liquid-absorbent core of which the absorption rate is low but the retention efficiency is high is used, urine leak from the diaper 10 can be further effectively prevented.

The liquid-absorbent structure 70 is bonded at the first bonded regions 81a, 81b and the second bonded regions 82 to the skin-contactable sheets 50 to be slung from the skin-contactable sheets 50 like a hammock and the space 42 is maintained between the liquid-absorbent structure 70 and the outer sheet 60 unless the space 42 collapses when the wearer gets seated. Even if the space 42 temporarily collapses under a body weight of the wearer getting seated, the space 42 once having collapsed is formed again as the wearer stands up.

Even when the weight of the liquid-absorbent structure 70 increases due to urine absorbed therein, the space 42 is maintained between the structure 70 and the outer sheet 60 because the structure 70 is slung from the skin-contactable sheets 50 like a hammock. The space 42 well maintained in this manner can reliably retain the inflow of urine which, in turn, can be absorbed by a still fresh part of the liquid-absorbent core 71. In this way, the liquid-absorbent core 71 as a whole can be efficiently used and thereby a volume of the liquid-absorbent core 71 can be reduced to the minimum necessary. The outer sheet 60 is adequately liquid-impervious to assure that urine reliably retained in the space 42. In response to movement such as walking of the wearer, such urine also moves within the space 42, comes in contact with the still fresh part of the liquid-absorbent core 71 and can be absorbed by this part.

The liquid-absorbent structure 70 is adapted to absorb urine not only through the surface thereof facing the skin-contactable sheets 50 but also through the surface thereof facing the outer sheet 60 whereby to improve its absorption rate and to achieve efficient use of the liquid-absorbent core 71. The skin-contactable sheets 50 and the outer sheet 60 both being liquid-impervious allow the inflow of urine to be retained within the space 42 defined by these sheets and thereby to prevent urine leak from the diaper 10.

While the inner side edges 53 of the respective skin-contactable sheets 50 define the opening 41 as a liquid-pervious region for bodily fluids in this Embodiment 1, it is also possible to define such liquid-pervious region by making the skin-contactable sheets 50 at least partially of a liquid-pervious fibrous non-woven fabric or the like. While the skin-contactable sheets 50 and the outer sheet 60 are formed of separate sheets and bonded together along the respective side edges in Embodiment 1, it is possible to form the skin-contactable sheets 50 and the outer sheet 60 from the one and same continuous sheet.

While the crotch elastic members 55 are used as separator means to make the length dimension of the respective skin-contactable sheets 50 in the longitudinal direction Y substantially smaller than that of the outer sheet 60 according to this Embodiment 1, it is possible to achieve such purpose by subjecting the outer sheet 60 to a stretching process so that the outer sheet 60 would be stretchable in the longitudinal direction Y. It is also possible to interpose a separate sheet between the skin-contactable sheets 50 and the outer sheet 60 and thereby to space the outer sheet 60 from the skin-contactable sheets 50.

[Embodiment 2]

Figure 4:
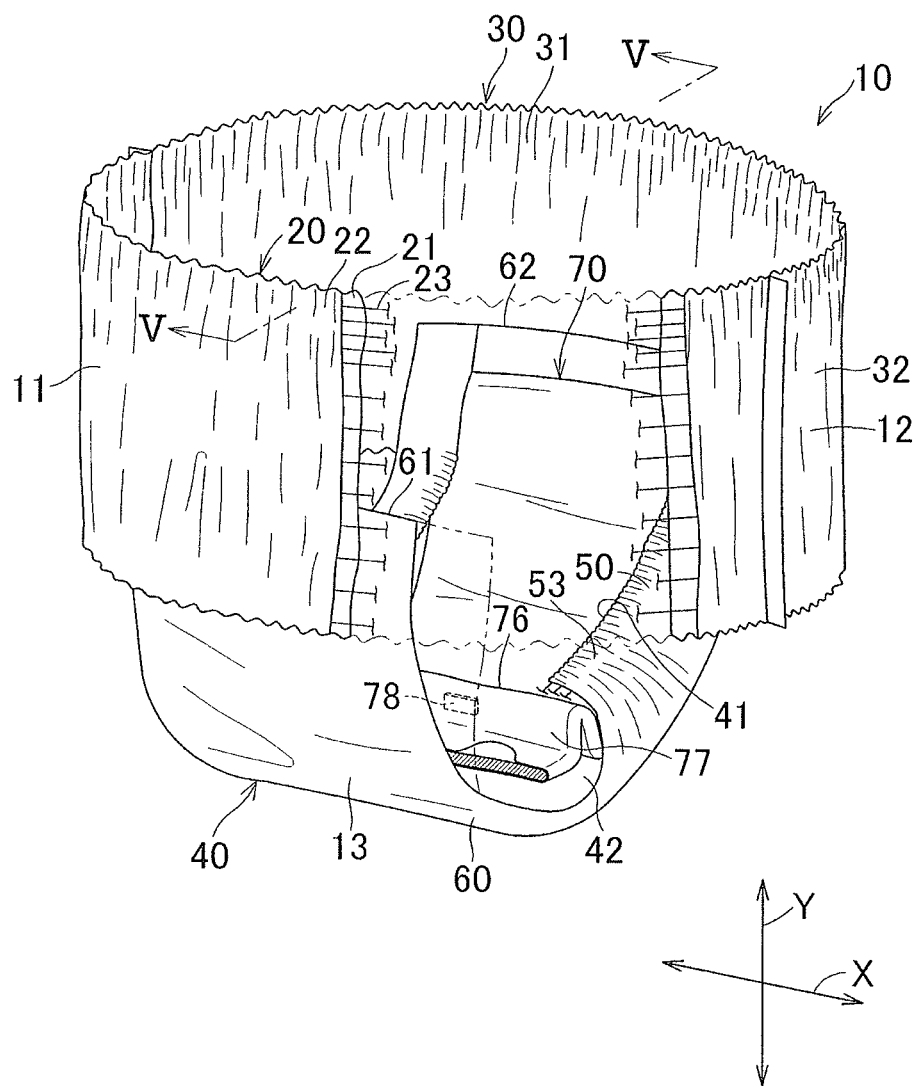
{FIG 4} A perspective view showing the diaper according to Embodiment 2.
Figure 5:
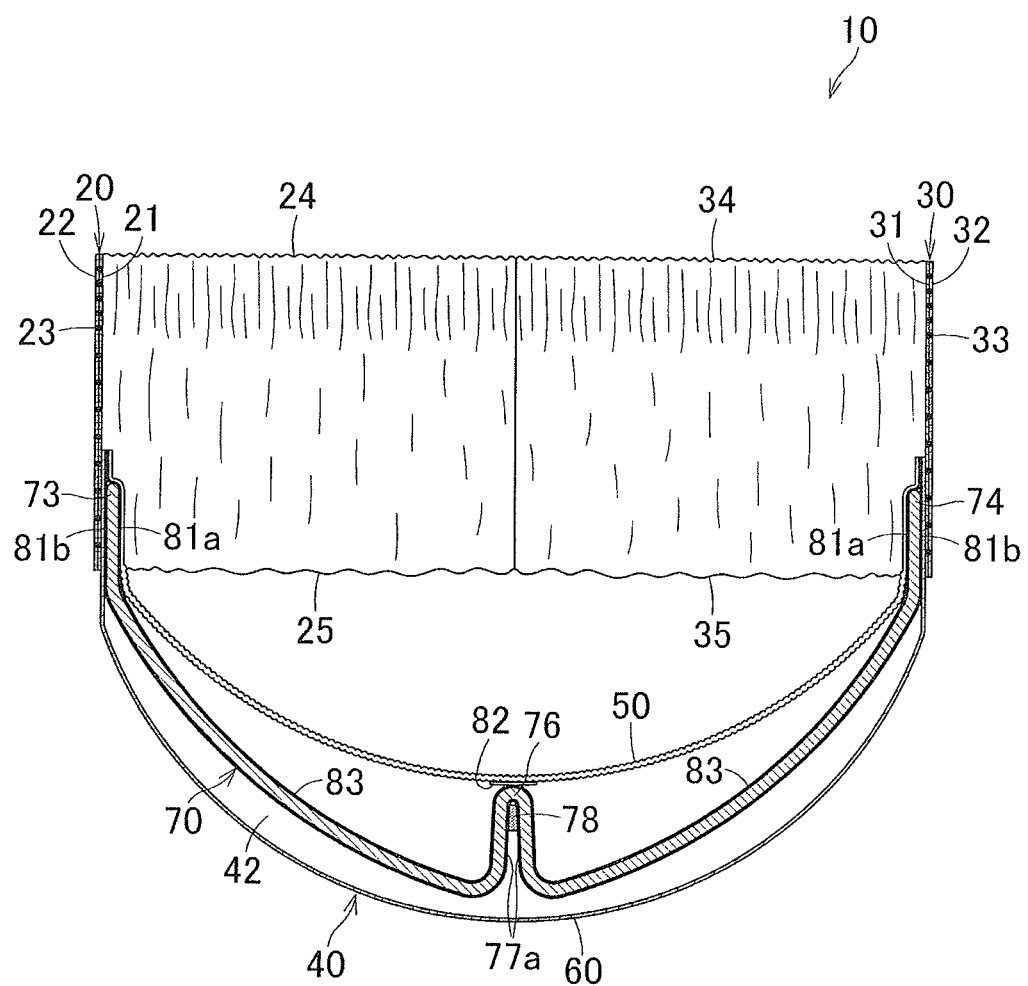
{FIG 5} A sectional view taken along the line V-V in FIG. 4.
Figure 6:
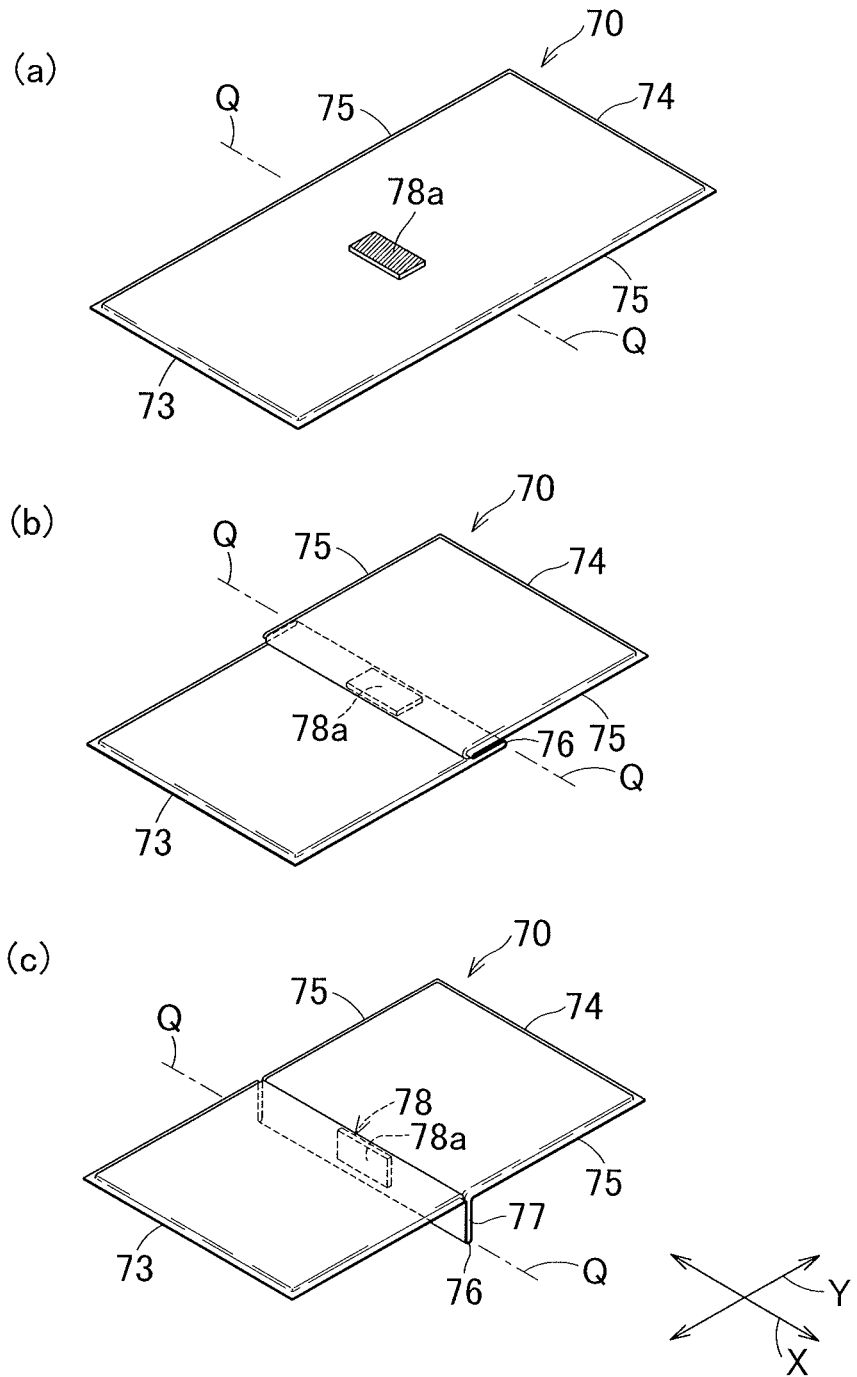
{FIG 6} (a)-(c) illustrates the liquid-absorbent structure of the diaper shown in FIG. 5.

FIGS. 4 through 6 illustrate Embodiment 2 of the present invention wherein FIG. 4 is a view similar to FIG. 1, showing the diaper as put on the wearer's body, FIG. 5 is a sectional view taken along the line V-V in FIG. 4 and FIG. 6 illustrates construction of the liquid-absorbent structure.

In view of the fact that front and rear waist members 20, as well as a crotch member 40 are similar to those in Embodiment 1, these similar members are designated by the same reference numerals as those used in illustration of Embodiment 1 and details of these members will not be repetitively described. Embodiment 2 is characterized in that a liquid-absorbent structure 70 is formed along a folding line 76 with a fold 77 and respective halves of the fold's inner surface 77a opposed to each other are bonded together.

As will be apparent from FIGS. 4 and 5, two halves of an inner surface 77a of a fold 77 opposed to each other are bonded together at a fold-bonding region 78 defined substantially in a middle of the liquid-absorbent structure 70 as viewed in the transverse direction X and the opposed halves of the fold's inner surface 77a are bonded to each other only in this fold-bonding region 78.

Now a method of forming the liquid-absorbent structure 70 with the fold-bonding region 78 will be described. Referring to FIG. 6A, the liquid-absorbent structure 70 is coated on one side thereof with bonding means 78a such as hot melt adhesive. This bonding means 78a is formed along a transverse center line Q-Q bisecting a length dimension of the liquid-absorbent structure 70 in the longitudinal direction Y and this coated region is length-dimensioned to be about 50 mm in the longitudinal direction Y and about 70 mm in the transverse direction X.

Referring now to FIG. 6B, the liquid-absorbent structure 70 is folded on the side thereof coated with the bonding means 78a along the transverse center line Q-Q and then folded in the opposite direction so that two halves of the fold's inner surface 77a opposed to each other would be bonded to each other by the bonding means 78a. Referring now to FIG. 6C, opposed surfaces of the fold 77 is bonded to each other by the bonding means 78a and the fold-bonding region 78 is formed. Along the transverse center line Q-Q, a folding line 76 is formed so that the halves of the fold's inner surfaces 77a are opposed to each other about this folding line 76.

Such liquid-absorbent structure 70 is bonded to the skin-contactable sheets 50 along the folding line 76 to form second bonded regions 82 (See FIGS. 4 and 5). The front and rear ends 73, 74 of the liquid-absorbent structure 70 are respectively sandwiched and bonded between the associated front and rear ends of the skin-contactable sheets 50 and the outer sheet 60 so that the fold 77 would hang down toward the outer sheet 60 and partition a space 42 defined between the skin-contactable sheets 50 and the outer sheet 60 into front and rear halves. By partitioning the space 42 into the front and rear halves in this manner, urine and feces can be separately retained by the front and rear halves of the space 42, respectively.

The fold-bonding region 78 of the liquid-absorbent structure 70 holds the fold's inner surface 77a having the opposed halves firmly bonded to each other and thereby locally increases partial stiffness of the liquid-absorbent structure 70. With the stiffness increased in this manner, the fold's inner surface 77a functions as spacer means to keep the skin-contactable sheets 50 and the outer sheet 60 spaced from each other even when these sheets 50, 60 are forced to move closer to each other.

Furthermore, the fold's inner surface 77a having its opposed halves bonded together in this manner facilitates the substantial length dimension of the liquid-absorbent structure 70 in the longitudinal direction Y to be set and thereby allows the dimensional relation between the skin-contactable sheets 50 and the outer sheet 60 to be reliably maintained.

While the fold-bonding region 78 of the liquid-absorbent structure 70 is formed only in the vicinity of the middle of the structure in the transverse direction X in this Embodiment 2, the fold-bonding region 78 is formed to extend across the structure 70 along its entire dimension in the transverse direction X. While specific dimensions of the fold-bonding region 78 have been exemplarily indicated above, the invention is not limited to these specific dimensions which may be, in turn, appropriately varied without departing from the scope of the invention. While use of adhesive as the bonding means 78a has been exemplarily described, it is possible to use the technique of well known in the relevant field such as thermal bonding or ultrasonic bonding.

[Embodiment 3]

Figure 7:
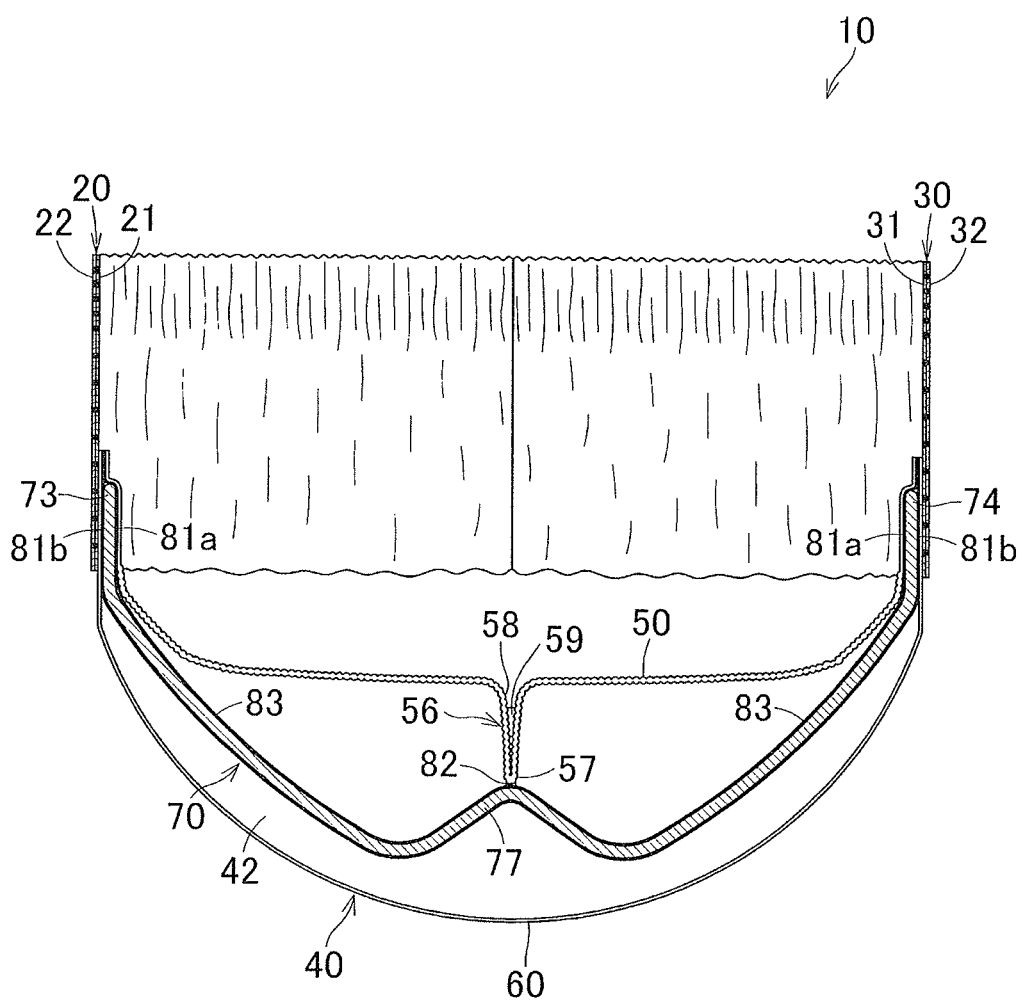
{FIG 7} A view similar to FIG. 2, showing the diaper according to Embodiment 3.

FIG. 7 illustrates Embodiment 3 of the present invention. FIG. 7 is a view similar to FIG. 2 and the components similar to those of Embodiment 1 will not be repetitively described hereunder. This Embodiment 3 is characterized in that skin-contactable sheets 50 are formed with folds 56 as spacer means adapted to substantially reduce a length dimension of the respective skin-contactable sheets 50 in the longitudinal direction Y and thereby to form a space 42 between the skin-contactable sheets 50 and the outer sheet 60.

Length dimension of the respective skin-contactable sheets 50 is set to be the same as that of the outer sheet 60 in the state that fold-bonding regions 59 of the skin-contactable sheets 50 are released and contractile force of respective elastic members is completely restricted. The respective skin-contactable sheets 50 are formed in a crotch region 13 with folds 56 so that the length dimension of the respective skin-contactable sheets 50 in the longitudinal direction Y would be substantially reduced. Specifically, the respective skin-contactable sheets 50 are folded along a folding line 57 extending in the transverse direction X to form respective folds 56. The respective folds 56 has opposed inner surface 58 facing the side of the wearer's skin and extending upward from the associated folding lines 57 toward the wearer's skin. The opposed halves of the inner surface 58 in the respective folds 56 are bonded together in the respective fold-bonding regions 59.

The liquid-absorbent structure 70 is formed with a fold 77 and the skin-facing side of this fold 77 is bonded to the folding lines 57 of the respective skin-contactable sheets 50 in second boding regions. By bonding the liquid-absorbent structure 70 to the respective skin-contactable sheets 50 in this manner, the liquid-absorbent structure 70 can be slung down from the skin-contactable sheets 50 like a hammock and thereby the space 42 can be maintained.

According to this Embodiment 3, by forming the respective skin-contactable sheets 50 with the folds 56, the substantial length dimension of the respective skin-contactable sheets 50 in the longitudinal direction Y can be reduced and no separate spacer means such as elastic members for the crotch region is necessary. As a consequence, the number of parts can be correspondingly reduced.

The opposed halves of the inner surface 58 in each of the folds 56 formed in the respective skin-contactable sheets 50 are bonded together in a fold-bonding region 59 so that the length dimension of the respective skin-contactable sheets 50 in the longitudinal direction Y would be maintained substantially reduced and thereby the space 42 would be maintained.

{Embodiment 4}

Figure 8:
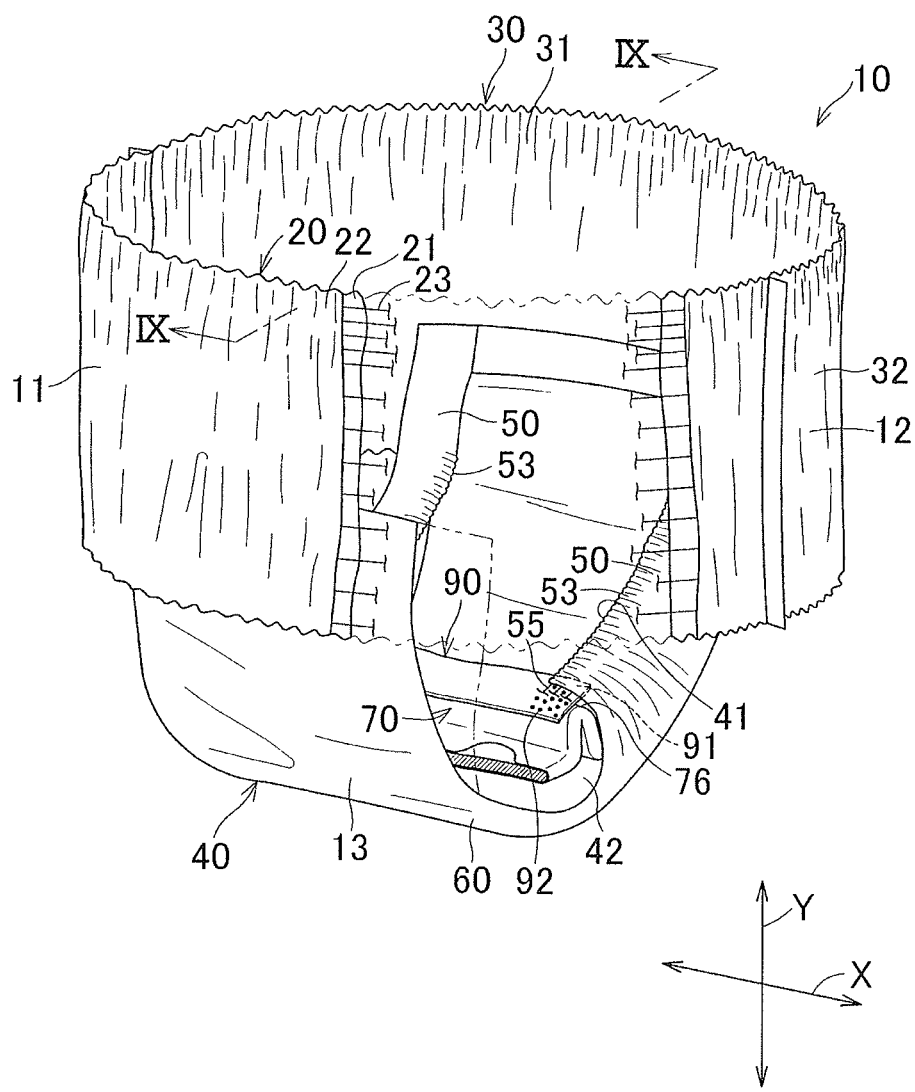
{FIG 8} A perspective view showing the diaper according to Embodiment 4.
Figure 9:
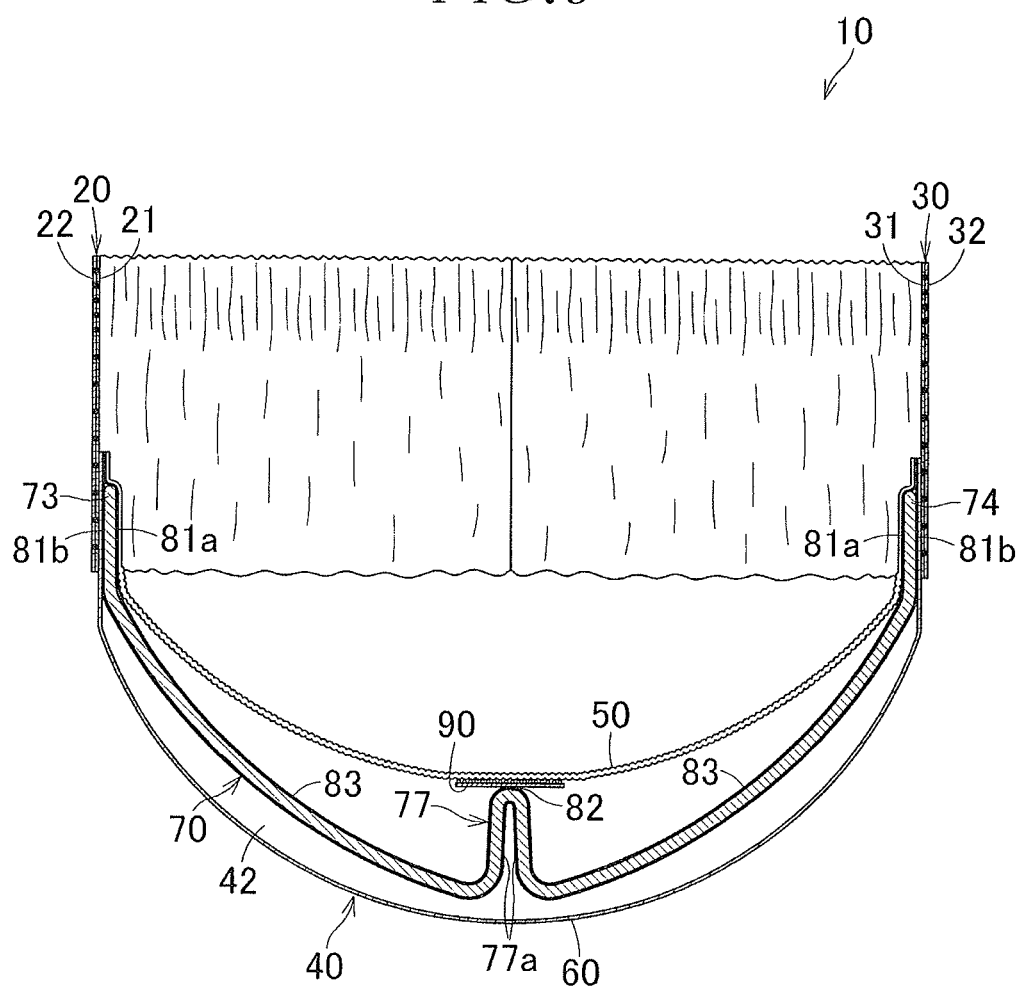
{FIG 9} A sectional view taken along the line IX-IX in FIG. 8.
Figure 10:
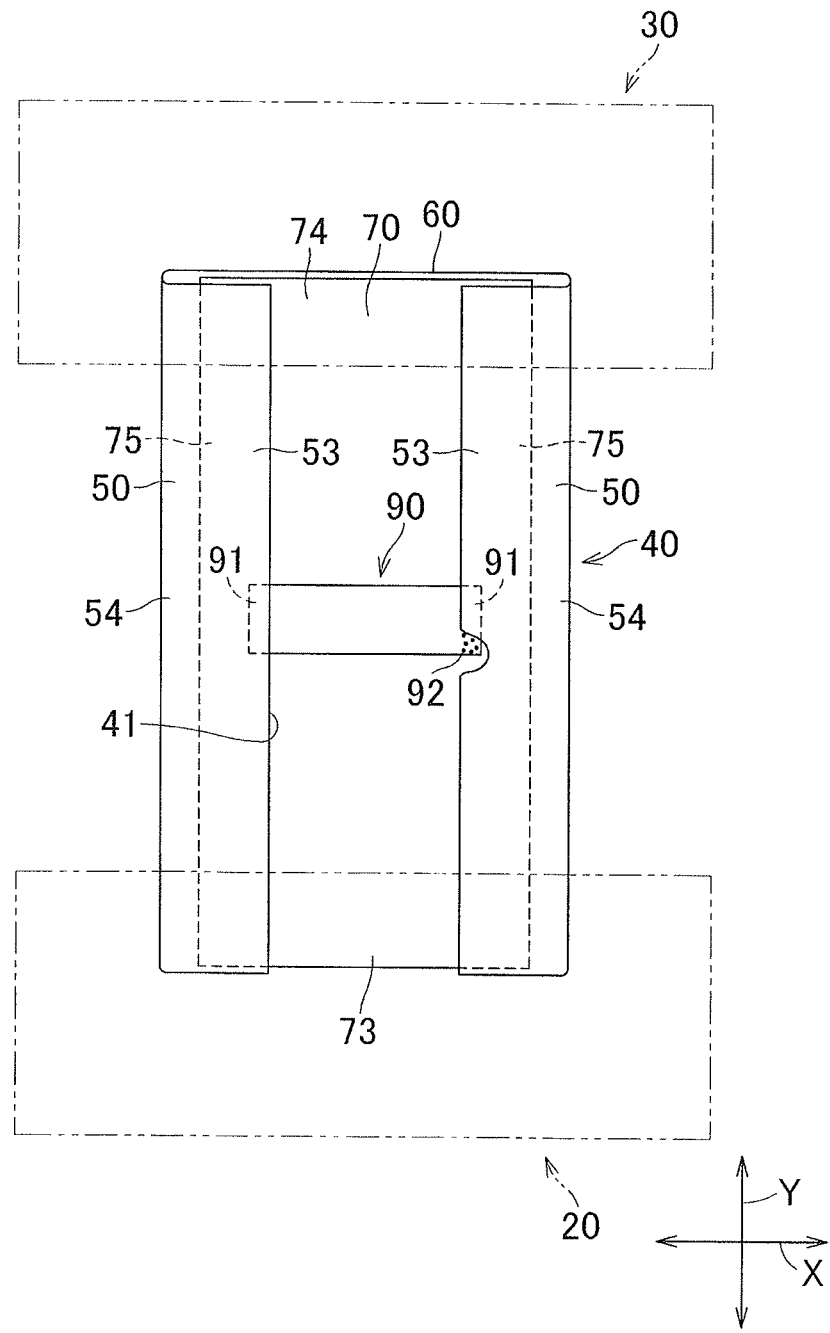
{FIG 10} A plan view showing a part of the diaper shown in FIG. 8 as having been flatly developed.

FIGS. 8 through 10 illustrate Embodiment 4 of the present invention wherein FIG. 8 is a view similar to FIG. 1, showing the diaper as put on the wearer's body, FIG. 9 is a sectional view taken along the line IX-IX in FIG. 8 and FIG. 10 is a view similar to FIG. 3 from which front and rear waist members 20, are eliminated. In view of the fact that the front and rear waist members 20, 30 in this Embodiment 4 are similar to those in Embodiment 1, no detailed description of these members will be repeated hereunder and only a crotch member 40 will be described. This Embodiment 4 is characterized in that a connector 90 is provided to connect a pair of skin-contactable sheets 50 to each other.

A pair of the skin-contactable sheets 50 spaced from each other in the transverse direction X define an opening 41 between respective inner side edges 53 and the connector 90 extends across the opening 41 in the transverse direction X to connect transversely opposite points on a periphery of the opening. More specifically, opposite side edges 91 of the connector 90 extending in the longitudinal direction Y are bonded in respective bonded zones 92 to the associated inner side edges 53 of the respective skin-contactable sheets 50 on the garment-facing side thereof, i.e., on the side thereof facing the outer sheet 60. The connector 90 fixes a pair of mutually spaced skin-contactable sheets 50 to a predetermined positional relation in this way and prevent the initial distance between them in the transverse direction X from being further enlarged until the opening 41 loses its initial shape. Should the skin-contactable sheets 50 be further spaced from each other, a distance between the skin-contactable sheets 50 and the outer sheet 60 maintained under the effect of the crotch elastic members 55 might be reduced and eventually a volume of the opening 41 might be reduced. However, the presence of the connector 90 allows the desired volume and shape of the space 42 to be maintained. So far as the space 42 can be maintained in its desired condition, the liquid-absorbent structure 70 can be maintained as slung within the space 42 and the liquid-absorbent structure 70 would not fall off onto the outer sheet 60.

When the connector 90 is provided as in this Embodiment 4, the liquid-absorbent structure 70 may be bonded along the folding line 76 to the connector 90 to define a second bonded region 82 extending over an entire area of the folding line 76 in the transverse direction X and thereby to maximize a joint area. Specifically, if such connector 90 is not provided, the second bonded regions 82 will be respectively formed on the respective skin-contactable sheets 50 i.e., opposite ends of the folding line 76 as viewed in the transverse direction X. On the contrary, the presence of the connector 90 allows the second bonded region 82 extending over the entire area of the folding line 76 in the transverse direction X. In this way, the liquid-absorbent structure 70 can be reliably raised toward the side of the skin-contactable structures 50 in the crotch region 13 and thereby the space can be maintained between the liquid-absorbent structure 70 and the outer sheet 60.

For reliable joint between the folding line 76 and the connector 90, it is essential that the folding line 76 and the connector 90 are opposed to each other in the thickness direction.

It is also possible to provide the connector 90 with an elastic member extending in the transverse direction X. Such elastic member may be attached under tension and in contractible fashion to the connector 90 so that the contractile force of this elastic member further assure the space defined by the skin-contactable sheets 50 and the outer sheet 60 to be maintained.

As the connector 90, for example, liquid-pervious fibrous non-woven fabric or liquid-impervious film sheet may be used. While it is also possible to bond the connector 90 to the skin-facing side of the skin-contactable sheets 50, the connector 90 is preferably positioned on the garment-facing side of the skin-contactable sheets 50 in order to alleviate uncomfortable irritation to the wearer's skin.

REFERENCE SIGNS LIST 10 diaper (absorbent article)
11 front waist region
12 rear waist region
13 crotch region
41 opening
42 space
50 skin-contactable sheet
55 elastic members for crotch region
60 back-sheet
70 liquid-absorbent structure
71 liquid-absorbent core
73 front end of liquid-absorbent structure
74 rear end of liquid-absorbent structure
75 side edges of liquid-absorbent structure
76 folding line
77a inner surface of fold
78 bonded region of liquid-absorbent structure
81a first bonded region
82 second bonded region
83 non-bonded region
90 connector member

The invention claimed is:

1. An absorbent article having a longitudinal direction and a transverse direction, said absorbent article comprising:
a chassis comprising a skin-facing side, a non-skin-facing side, a front waist region, a rear waist region and a crotch region extending between the front and rear waist regions; and
a liquid-absorbent structure extending at least in the crotch region to absorb bodily fluids and comprising a liquid-absorbent core and a liquid-pervious wrapping sheet wrapping the liquid-absorbent core,
wherein
the chassis further comprises
a skin-contactable sheet lying on the skin-facing side to define at least the crotch region and formed with a liquid-pervious region,
a liquid-impervious outer sheet lying on the non-skin-facing side, and
a spacer configured to space the skin-contactable sheet from the outer sheet and thereby to define a space therebetween,
the liquid-absorbent structure is positioned within the space and connected to the skin-contactable sheet in alignment with the liquid-pervious region in a thickness direction,
a part of the liquid-absorbent structure is configured to come in contact with the outer sheet,
said liquid-absorbent structure includes
a fold formed along a folding line extending in said transverse direction, and
a fold-bonding region on a surface on the non-skin-facing side of said fold, and the surface of said fold has mutually opposed halves bonded together in said fold-bonding region, wherein
a length dimension of the liquid-absorbent structure in the longitudinal direction is substantially larger than a length dimension of the skin-contactable sheet in the longitudinal direction and substantially smaller than a length dimension of the outer sheet in the longitudinal direction, and
the liquid-absorbent structure further includes
front and rear ends extending in the transverse direction and formed with first bonded regions in which the liquid-absorbent structure is bonded to the skin-contactable sheet, and
side edges extending in the longitudinal direction and formed with non-bonded regions in which the liquid-absorbent structure is configured to be spaced from the skin-contactable sheet.

2. The absorbent article defined by claim 1, wherein a substantial length dimension of the skin-contactable sheet in the longitudinal direction is smaller than a length dimension of the outer sheet in the longitudinal direction under the effect of the spacer.

3. The absorbent article defined by claim 1, wherein
the liquid-pervious region is defined by an opening formed in the skin-contactable sheet; and
the skin-contactable sheet is elasticized along the opening at least in the longitudinal direction under the effect of the spacer.

4. The absorbent article defined by claim 1,
wherein the liquid-absorbent structure is formed along the side edges thereof with second bonded regions lying in the crotch region, and
wherein the liquid-absorbent structure is bonded to the skin-contactable sheet in the second bonded regions.

5. The absorbent article defined by claim 1, wherein the fold is formed in the crotch region to extend toward the skin-contactable sheet in the thickness direction.

6. The absorbent article defined by claim 1,
further comprising a connector extending across the opening in the transverse direction and connecting transversely opposite portions of a periphery of the opening.

7. The absorbent article defined by claim 6, wherein the connector lies at least in the crotch region.

8. The absorbent article defined by claim 6, wherein the fold-bonding region of said liquid-absorbent structure overlaps the connector in the thickness direction.

9. The absorbent article defined by claim 1, wherein an inner side edge between front and rear ends of the skin-contactable sheet is directly bonded to the liquid-absorbent structure.

10. The absorbent article defined by claim 1, wherein the liquid-absorbent structure is positioned within the space and directly connected to the skin-contactable sheet in alignment with the liquid-pervious region in the thickness direction.

11. The absorbent article defined by claim 1, wherein the liquid-absorbent structure is positioned within the space and indirectly connected to the skin-contactable sheet in alignment with the liquid-pervious region in the thickness direction.

12. The absorbent article defined by claim 4, wherein the second bonded regions are positioned between the non-bonded regions in the longitudinal direction.

* * * * *